United States Patent [19]
Sopori

[11] Patent Number: 5,406,367
[45] Date of Patent: Apr. 11, 1995

[54] DEFECT MAPPING SYSTEM

[75] Inventor: Bhushan L. Sopori, Denver, Colo.

[73] Assignee: Midwest Research Institute, Kansas City, Mo.

[21] Appl. No.: 60,301

[22] Filed: May 10, 1993

[51] Int. Cl.[6] ............................................. G01N 21/88
[52] U.S. Cl. ......................................... 356/30; 356/36; 356/237; 356/446
[58] Field of Search ................... 356/30, 31, 237, 446, 356/371, 36

[56] References Cited

U.S. PATENT DOCUMENTS

| | | |
|---|---|---|
| 4,243,473 | 6/1981 | Yamaguchi et al. . |
| 4,449,818 | 5/1984 | Yamaguchi et al. ................ 356/237 |
| 4,482,245 | 11/1984 | Makabe et al. . |
| 4,626,101 | 12/1986 | Ogawa et al. . |
| 4,794,265 | 12/1988 | Quackenbos et al. . |
| 4,840,487 | 6/1989 | Noguchi et al. . |
| 4,925,298 | 5/1990 | Dobrilla . |
| 5,008,542 | 4/1991 | Look et al. . |

FOREIGN PATENT DOCUMENTS 119439  5/1987  Japan ..................................... 356/30

OTHER PUBLICATIONS

B. L. Sopori, Use of Optical Scattering to Characterize Dislocations Semiconductors, 22 Appl. Optics 4676 (1988).

Primary Examiner—F. L. Evans
Attorney, Agent, or Firm—Ken Richardson; Edna M. O'Connor

[57] ABSTRACT

Apparatus for detecting and mapping defects in the surfaces of polycrystalline materials in a manner that distinguishes dislocation pits from grain boundaries includes a laser for illuminating a wide spot on the surface of the material, a light integrating sphere with apertures for capturing light scattered by etched dislocation pits in an intermediate range away from specular reflection while allowing light scattered by etched grain boundaries in a near range from specular reflection to pass through, and optical detection devices for detecting and measuring intensities of the respective intermediate scattered light and near specular scattered light. A center blocking aperture or filter can be used to screen out specular reflected light, which would be reflected by nondefect portions of the polycrystalline material surface. An X-Y translation stage for mounting the polycrystalline material and signal processing and computer equipment accommodate rastor mapping, recording, and displaying of respective dislocation and grain boundary defect densities. A special etch procedure is included, which prepares the polycrystalline material surface to produce distinguishable intermediate and near specular light scattering in patterns that have statistical relevance to the dislocation and grain boundary defect densities.

20 Claims, 12 Drawing Sheets

DEFECT MAPPING SYSTEM

The United States Government has rights in this invention under Contract No. DE-AC02-83CH10093 between the U.S. Department of Energy and the National Renewable Energy Laboratory, a Division of Midwest Research Institute.

BACKGROUND OF THE INVENTION

1. Field of the Invention

This invention is related generally to techniques for mapping defects on semiconductor surfaces and more particularly to an optical system that can distinguish dislocation pits from grain boundaries in mapping polycrystalline device surfaces.

2. Description of the Prior Art

The quality and suitability of crystalline and polycrystalline materials, such as silicon, gallium-arsenic, and others, for use as substrates for semiconductor applications are affected by defects, such as dislocations, in the crystalline structures. Generally, higher densities of dislocations are indicative of lower quality materials. Therefore, there is a need for systems to detect, measure, and map dislocation densities in crystalline and polycrystalline materials for purposes of analysis and quality control.

There are a number of systems that have been developed to detect and map dislocation densities. The methods used most commonly in the industry currently utilize a surface cleaning or polish step followed by some variation of an etch, which reveals dislocations that intersect the surface of the material by forming a pit at each dislocation site. The pits can then be detected, counted, and mapped, and the density of the pits, i.e., number of pits per unit of surface area, can be determined. This etch pit density (EPD) is considered by persons skilled in this art to be a reliable indicator of the number and density of dislocations in the substrate, and the pits have patterns that reflect slip planes in the crystal lattice of the material.

The most commonly used method of detecting and counting pits to determine EPD is visual observation through a microscope and counting. This process is obviously labor intensive, time consuming, and tedious work. Some alternative systems based on optical technologies to detect and map EPDs have been developed that apparently work on monocrystalline substrates, but none that work reliably for polycrystalline substrates. For example, the U.S. Pat. No. 4,925,298, issued to P. Dobrilla, compares specularly reflected light from an etched sample surface to light reflected from a reference surface to determine EPD. U.S. Pat. No. 5,008,542, issued to D. Look et al. is similar, except it detects light transmitted through the substrate rather than reflected light. In both of those techniques, the specular light is detected, so an increase of dislocation density results in increase of scattered light, and thus a decrease in detection signal. However, polycrystalline substrates present major problems for those systems, because grain boundaries cause substantial light scattering, thus affecting light detection signals and skewing EPD measurements.

It has also been shown and is now well-known in the industry that light scattering from a defect-etched surface can be used to determine surface dislocation numbers statistically. In fact, as reported in B. L. Sopori, "Use of optical scattering to characterize dislocations in semiconductors," 22 APPL OPTICS 4676 (1988), it has been determined that the total integrated light scattered from an illuminated region of a defect-etched surface is proportional to the number of dislocation etch pits in that area, provided that the surface is etched for defect delineation. A light integrating sphere positioned on the surface of the material collects and integrates substantially all of the scattered light, and a photodetector mounted in the integrating sphere measures the integrated light intensity, thus the extent of EPD in an illuminated area on the surface. Again, however, while that large beam statistical EPD detection and mapping technique works well for many applications involving single crystal materials, it does not work well with polycrystalline structures. Grain boundaries in polycrystalline materials are "grooved" in the defect etching process required for defect delineation, so scattering of light by the grain boundaries can cause a larger amplitude integrated light in the integrating sphere, and thus an erroneous EPD signal.

SUMMARY OF THE INVENTION

A general object of this invention, therefor, is to provide an improved defect mapping system for crystalline materials.

Another general object of this invention is to provide a defect mapping system that is useable and accurate on polycrystalline materials as well as crystalline materials.

A more specific object of this invention is to provide an optical scattering defect mapping system wherein light scattered by etched dislocation pits can be discriminated from light scattered by grain boundaries.

Another specific object of this invention is to provide an improvement to large beam statistical EPD detection and mapping systems that can be used on both single crystal and polycrystalline materials.

An even more specific object of this invention is to provide an improved large beam statistical EPD detection and mapping system that can be adjusted to detect and map either EPD or grain boundaries of a polycrystalline material.

Additional objects, advantages and novel features of this invention shall be set forth in part in the description that follows, and in part will become apparent to those skilled in the art upon examination of the following specification or may be learned by the practice of the invention. The objects and advantages of the invention may be realized and attained by means of the instrumentalities, combinations, and methods particularly pointed out in the appended claims.

To achieve the foregoing and other objects and in accordance with the purposes of the present invention, as embodied and broadly described therein, a defect mapping system includes a method for scattering light from the surface of a crystalline material that contains two types of defects, for example, dislocation defects and grain boundary defects, such that the first type of defect scatters light in a first pattern, and the second type of defect scatters light in a second pattern. The first type of pattern for dislocations produces a two-dimensional image with a light intense area surrounding a light void area. The second type of pattern for grain boundaries produces a practically one-dimensional image, some of which is distributed in the light void area of the first pattern and some of which extends through and beyond the light intense area of the first pattern. The light intense area of the first pattern is captured in a light integrating sphere for detection. The light of the second pattern that is near specular passed through the light integrating sphere for separate detection. Alternatively, the far specular dispersion of light in the second pattern can be diverted and detected in front of the light integrating sphere. The surface preparation that produces these distinct patterns of scattered light includes an etch procedure that creates etch pits at dislocation sites of about equal volume, regardless of dislocation orientation, and V-shaped grooves at grain boundaries.

BRIEF DESCRIPTION OF THE DRAWINGS

The file of this patent contains at least one drawing executed in color. Copies of this patent with color drawings will be provided by the Patent and Trademark Office upon request and payment of the necessary fee.

The accompanying drawings, which are incorporated in and form a part of the specifications, illustrate the preferred embodiments of the present invention, and together with the descriptions serve to explain the principles of the invention.

In the Drawings:

FIG. 4b is an illustration of the pattern of light scattered by a V-shaped etch grain boundary of FIG. 4a;

DETAILED DESCRIPTION OF THE PREFERRED EMBODIMENTS

Figure 1:
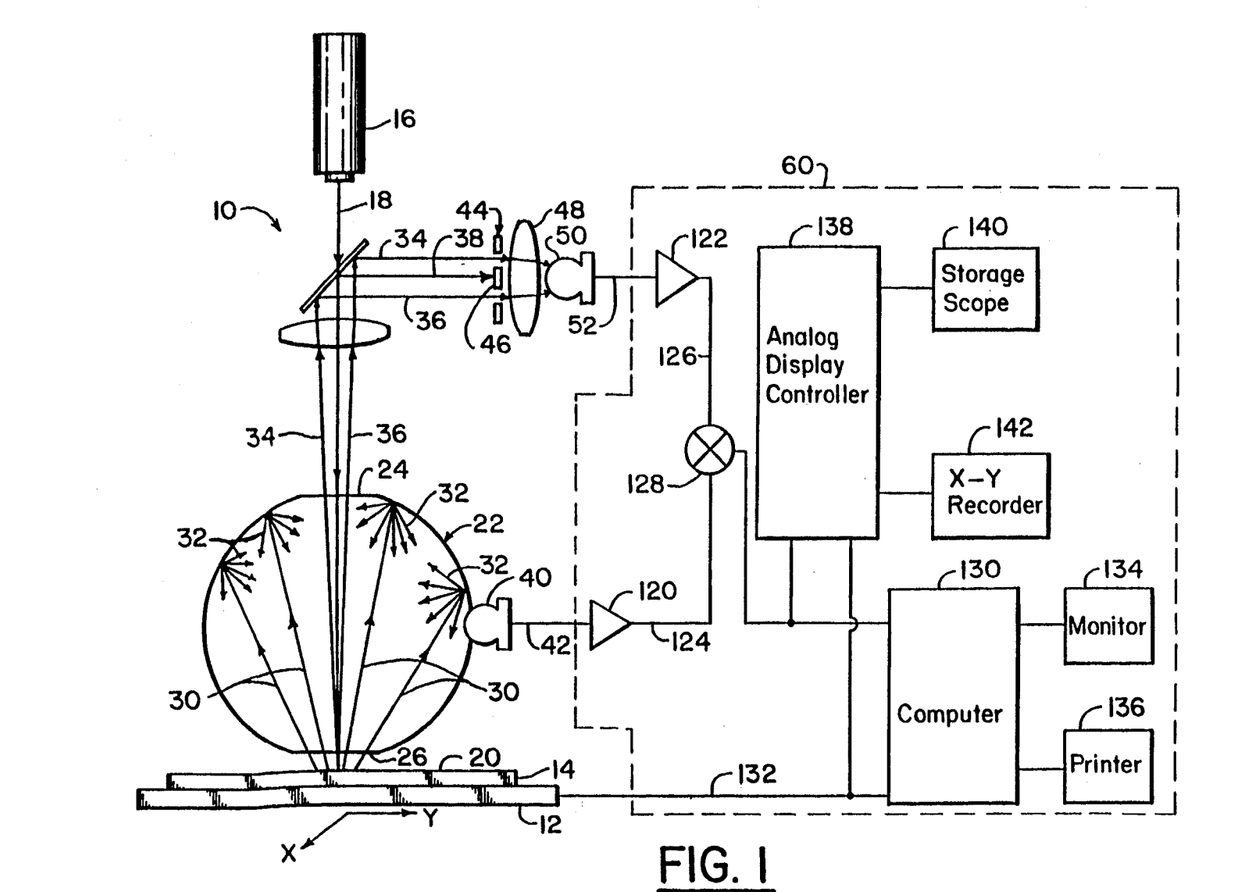
FIG. 1 is a schematic diagram of the improved defect mapping system of the present invention.

The improved defect mapping system 10 of this invention is illustrated schematically in FIG. 1. An X-Y translation stage 12 is provided for supporting a crystalline sample or substrate 14 positioned for defect detection and mapping according to this invention. A laser beam generator 16, such as a HeNe laser system capable of generating a laser beam 18 of light with a wavelength of approximately 6,382 Å, is positioned above the stage 12 and preferably oriented to direct a laser beam 18 perpendicularly onto the exposed surface 20 of crystalline material or sample 14.

Figure 8:
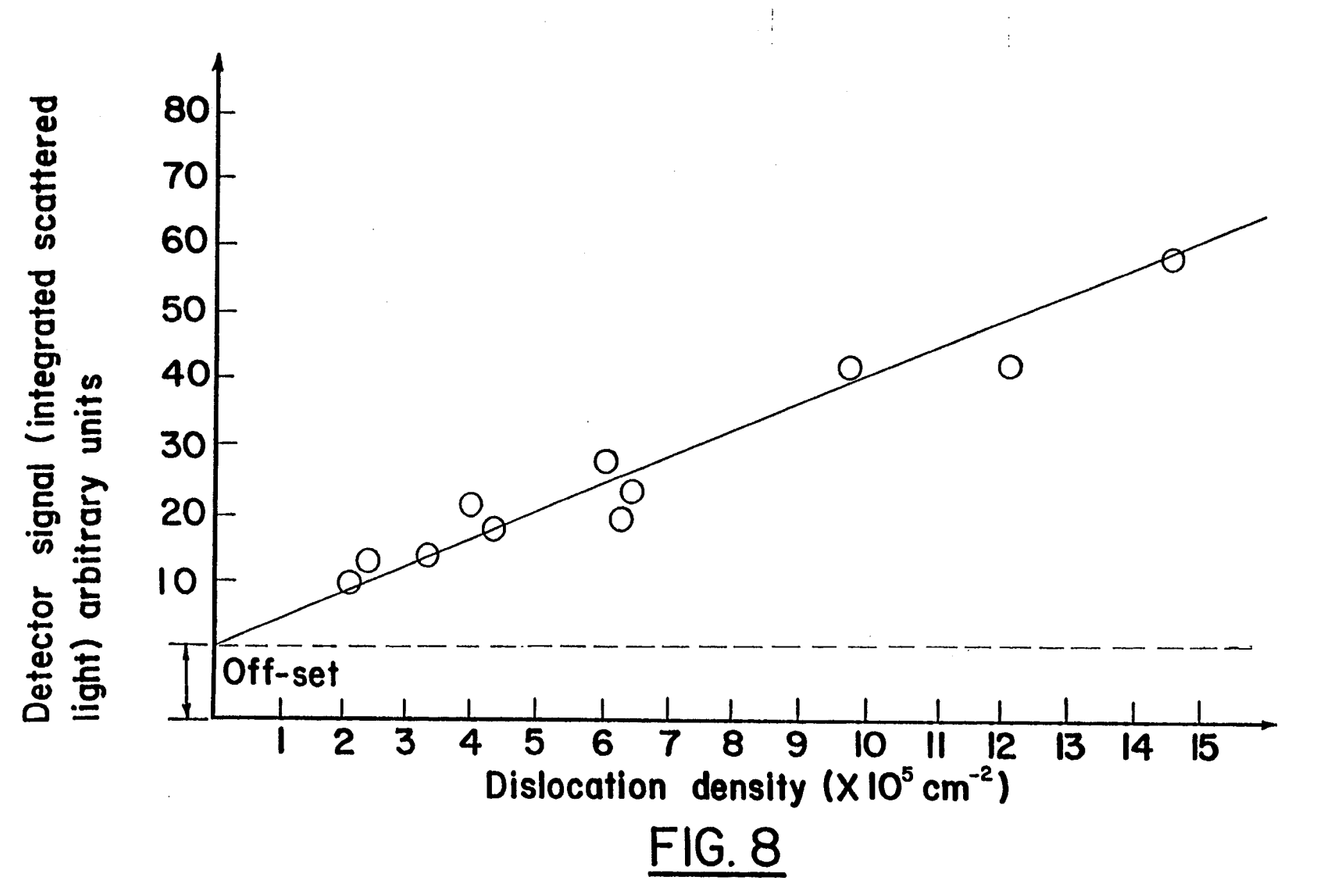
FIG. 8 is a graph of detector signal intensity (integrated scattered light) plotted versus dislocation density.

A light integrating sphere 22 has two diametrically opposed apertures 24, 26 positioned to allow transmission of the laser beam 18 through the light integrator sphere 22, when it is positioned between the laser generator 16 and the sample 14. However, the light integrator sphere 22 captures light rays 30 that are scattered by the surface 20 of sample 14 through the bottom aperture 26. The interior surface 28 of the integrator 22 is coated with a material, such as magnesium oxide, that enhances uniform scattering and integrated distribution or diffusion of light rays 30 captured therein through the bottom aperture 26, as illustrated at 32. A first photodetector 40 positioned in the side of the light integrator sphere 22 detects the intensity of diffused light 32 in the light integrating sphere 22 and produces an analog signal on lead 42 indicative of the diffused light 32 intensity. As illustrated in the graph in FIG. 8, and as will be discussed in more detail below, the intensity of the diffused or integrated scattered light 32 in FIG. 1, thus the amplitude of the signal produced on lead 42, is a direct measure of etched pit dislocation density (EPD) on the position of surface 20 of sample 14 that is illuminated by laser beam 18.

At the same time, the near specular components 34, 36 of light scattered by etched grain boundaries (not shown in FIG. 1, but described below) in the surface 20 of a polycrystalline sample 14, along with specular reflection 38, are allowed by bottom aperture 26 and top aperture 24 to pass through the light integrating sphere 22, as illustrated in FIG. 1. The specular component 38, which is primarily comprised of light reflected by smooth portions, i.e., non-defect portions, of the surface 20 of sample 14, is blocked and eliminated by an opaque center 46 of a center blocking aperture 44, while the near specular components 34, 36 are passed to a converging lens 48 and to a second photodetector 50. Since most of the light that reaches this second photodetector 50 is the near specular component of light scattered by etched grain boundaries, as will be described in more detail below, a strong electric signal produced on lead 52 by photodetector 50 indicates the presence of a grain boundary in the portion of the surface 20 of sample 14 that is illuminated by the laser beam 18.

The signal processing and control unit 60 shown in FIG. 1 processes and stores the signals from the photodetectors 40 and 50 in conjunction with X-Y position information of the stage 12, as the stage 12 rastors the sample 14 under the laser beam 18. Therefore, visual displays or other outputs of etch pit density (EPD) or grain boundary mapping can be produced for all or any desired portion of the surface 20 of sample 14.

Figure 3A:
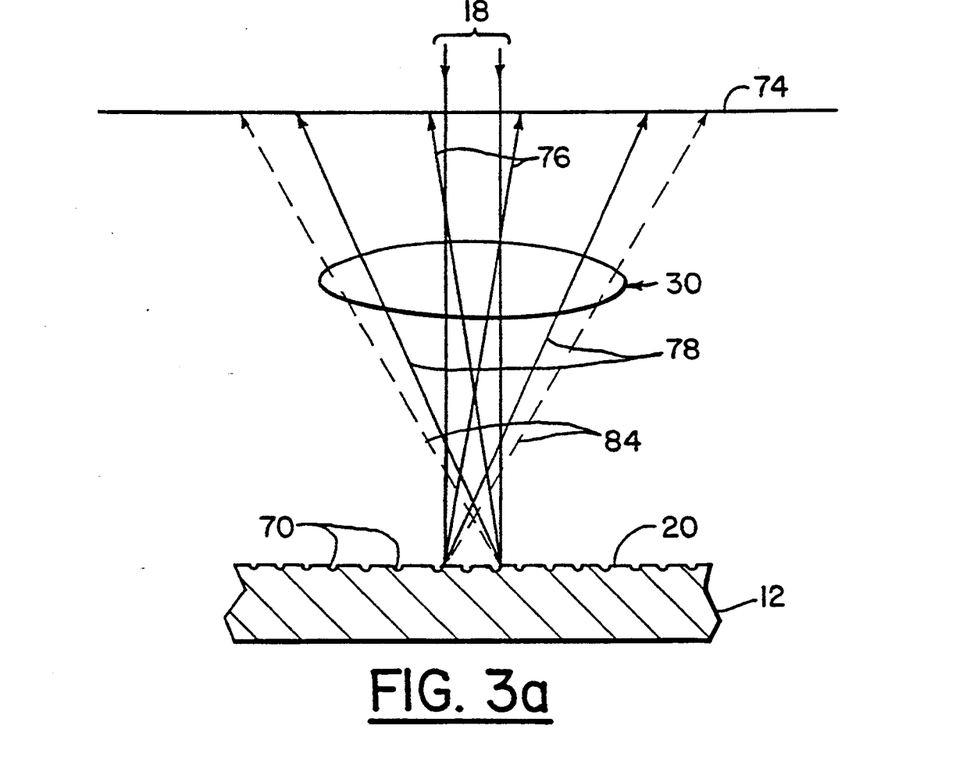
FIG. 3a is a schematic representation of the scattered light rays from an illuminated crystalline material sample that has an etched surface to reveal and delineate defects, particularly dislocations, in the crystalline material.
Figure 3B:
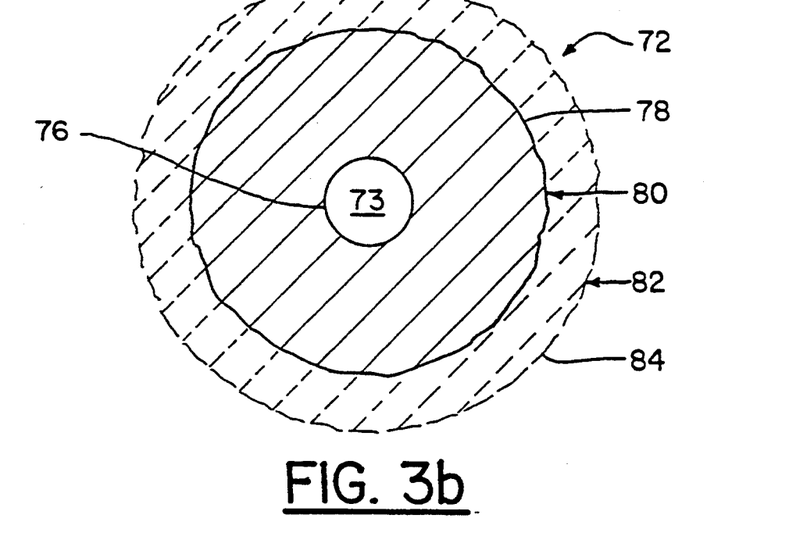
FIG. 3b is a representation of a typical scattered light pattern from an illuminated crystalline sample that has been etched according to this invention.

Referring now to FIGS. 3a and 3b, a crystalline sample 14 with etch pits 70 in the surface 20 where dislocation defects occur is shown illuminated by a laser beam 18. When properly etched, as will be described in more detail below, the etch pits 70 scatter the light in a definite and repeatable pattern 72 illustrated in FIG. 3b. The pattern 72 in FIG. 3b is the projection of the scattered light beams in FIG. 3a on the plane 74. Essentially, the etch pits 70 scatter most of the incident light from beam 18 in a conical pattern, as show in FIG. 3a, between about five degrees (5°) and twenty degrees (20°) from normal. The beams 76 illustrate the inner boundary of this range, and the beams 78 illustrate the outer boundary. Corresponding boundaries 76 and 78 define the primary high intensity light ring 80 of the resulting pattern 72 in FIG. 3b. A fringe ring 82 of less intensity surrounds the primary ring 80, as depicted by scattered fringe rays 84. The center circle 73 of pattern 72 is essentially devoid of scattered light from the etch pitted surface 20. All of the scattered light in the primary ring 80 and the fringe ring 82 of pattern 72 is collectively designated as the etch pit scattered light 30 for convenience in describing this invention.

Figure 3C:
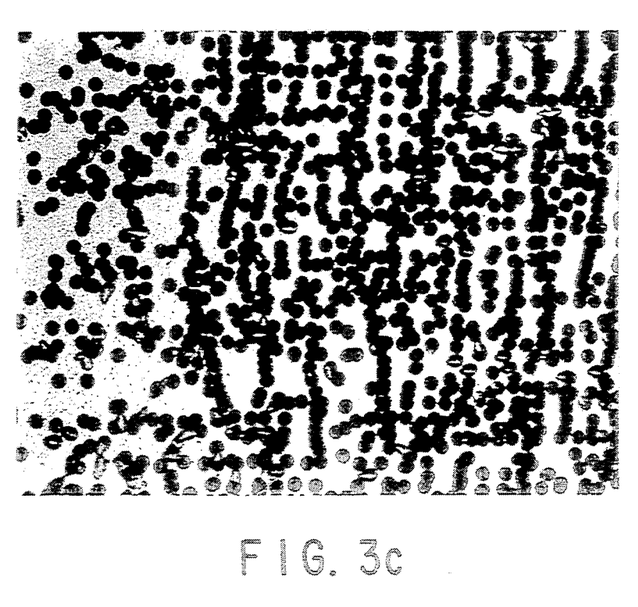
FIG. 3c is an enlarged view of etch pits on the surface of a silicon sample, wherein the etch pits are substantially circular in shape.
Figure 3D:
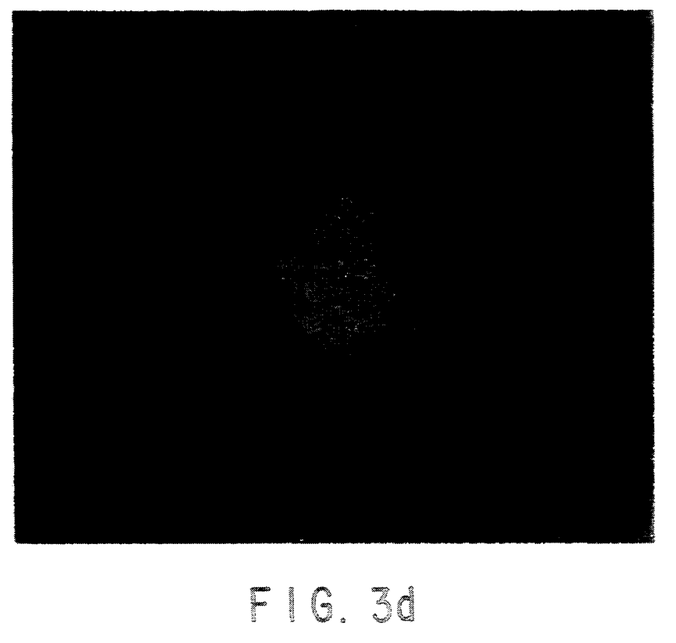
FIG. 3d is a photograph of an actual light pattern that has been scattered by the surface of the silicon sample of FIG. 3c according to this invention.
Figure 3E:
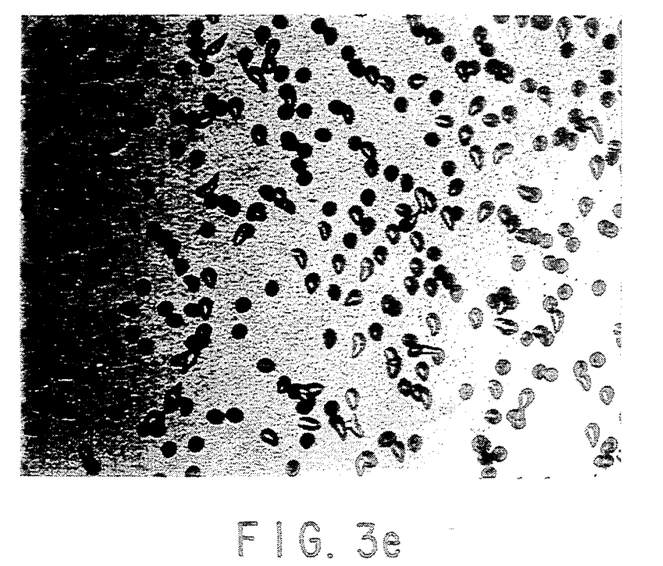
FIG. 3e is an enlarged view of etch pits on the surface of a silicon sample, wherein the etch pits are substantially elliptical in shape.
Figure 3F:
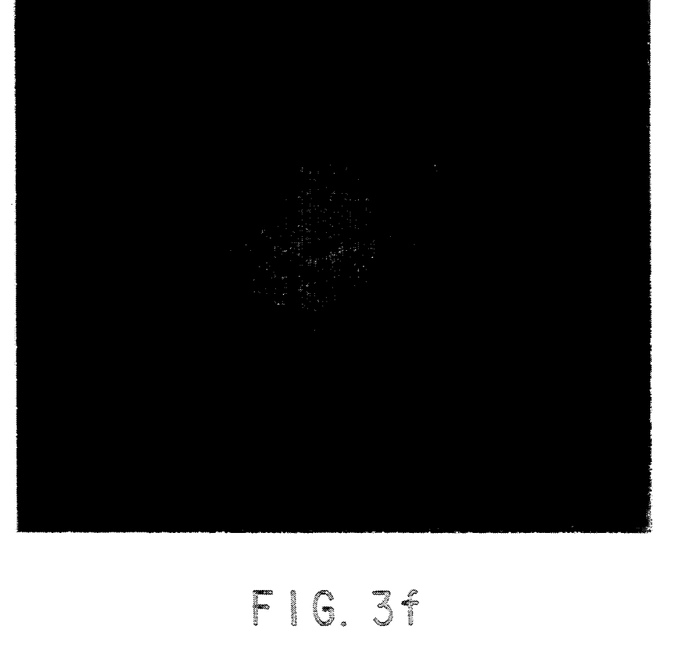
FIG. 3f is a photograph of an actual light pattern that has been scattered by the surface of the silicon sample of FIG. 3e.
Figure 3G:
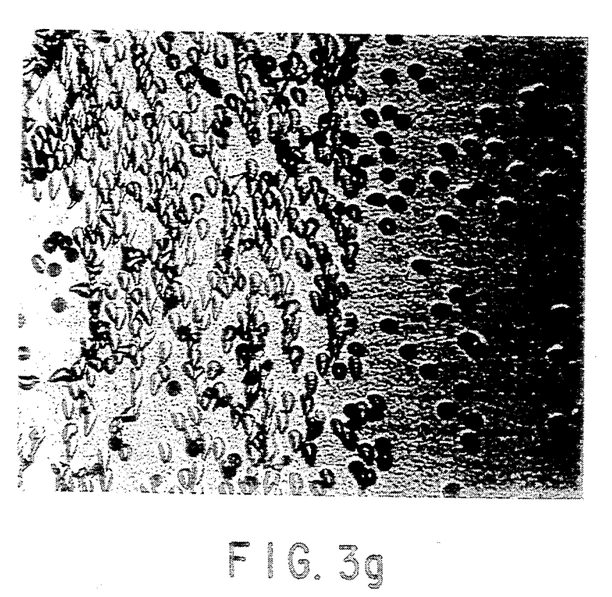
FIG. 3g is an enlarged view of etch pits on the surface of a silicon sample, wherein the etch pits are two different shapes (resembling ellipses)
Figure 3H:
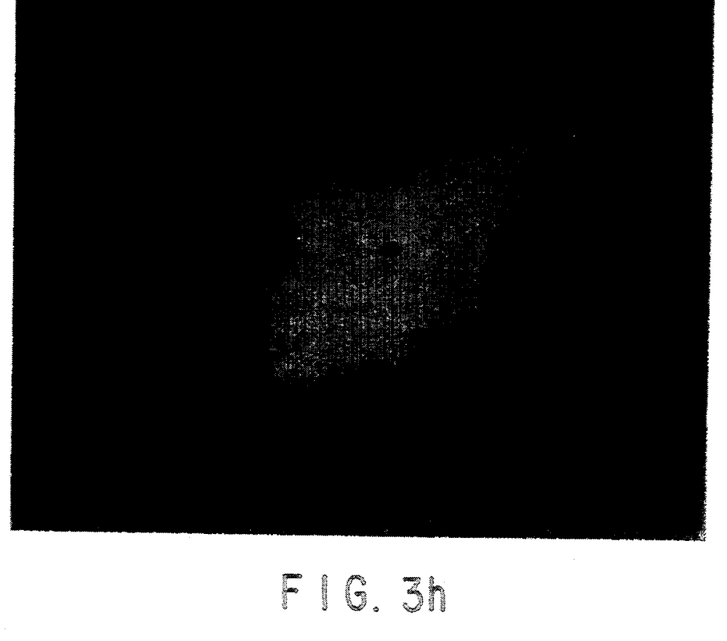
FIG. 3h is a photograph of an actual light pattern that has been scattered by the surface of the silicon sample of FIG. 3g.

FIG. 3d is an illustration of a pattern 72 produced by scattered light from the substantially circular shaped etch pits in FIG. 3c. Such circular shaped etch pits indicate dislocation defects that are oriented substantially normal to the surface, and, when etched as described below for this invention, will always produce the characteristic circular pattern of etch pit scattered light shown in FIG. 3d and depicted in FIG. 3b. In contact, dislocation defects that are oriented oblique to the surface produce elliptical shaped etch pits, as shown in FIG. 3e. Such elliptical etch pits produce an elliptical shaped pattern of etch pit scattered light, as shown in FIG. 3f. A mixed set of etch pits comprising both circular and elliptical shapes in close proximity, as shown in FIG. 3g, will produce an irregular shaped etch pit scattered light pattern, as shown in FIG. 3h.

Figure 2:
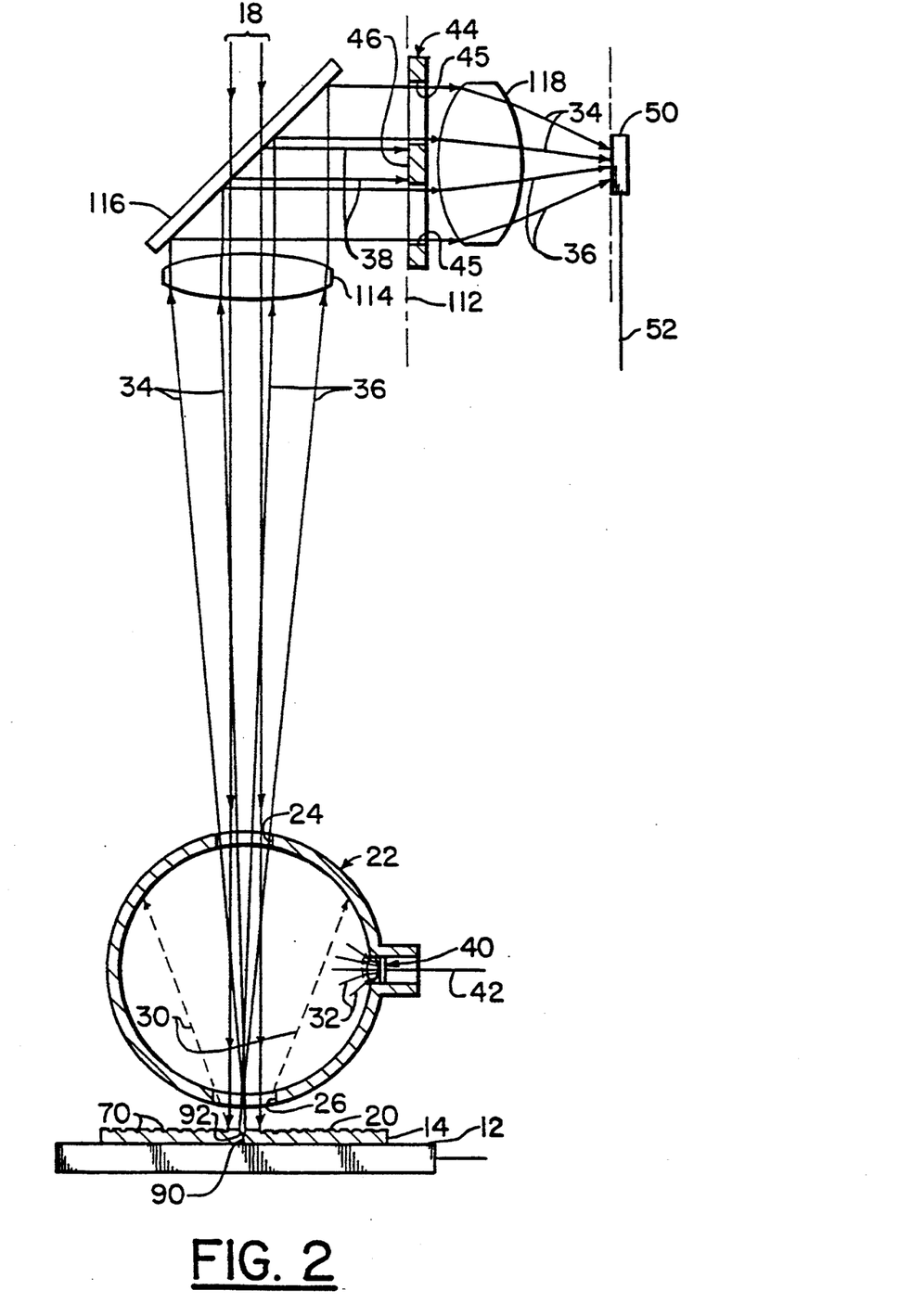
FIG. 2 is an enlarged schematic illustration of the optical components of the system shown in FIG. 1.

Referring now momentarily to FIGS. 1 and 2, the bottom aperture 26 of the light integrating sphere 22 is sized and positioned to admit most of the etch pit scattered light 30, for example, about 20 to 40 degrees from normal. The top aperture 24 is preferably sized and positioned to not allow light rays 30 scattered from the surface 20 wider than about five degrees from normal to pass therethrough. In other words, the top aperture 24 preferably coincides substantially with the void center circle 73 of the etch pit scattered light pattern 72 of FIG. 3b. Consequently, most of the etch pit scattered light 30 is captured and retained by light integral sphere 22 where it is integrated to produce intense diffuse light 32 to induce a strong signal from photodetector 40. At the same time, very little of the etch pit scattered light 30 escapes through top aperture 24 to reach the second photodetector 50, so any signal produced by photodetector 50 is not influenced significantly by etch pit scattered light 30.

Figure 4A:
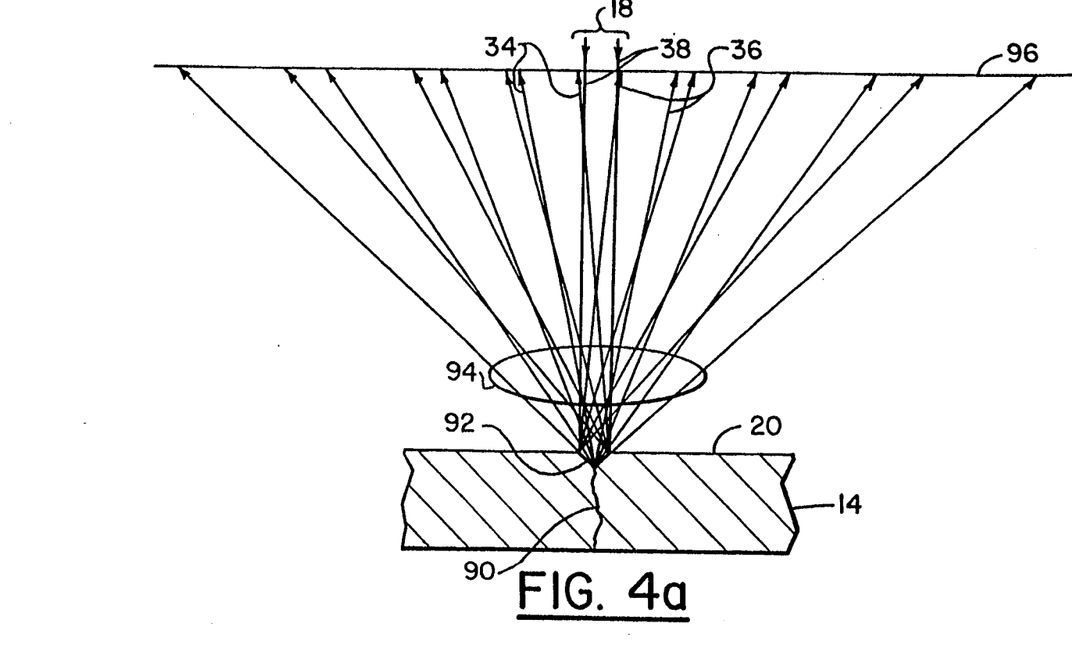
FIG. 4a is a schematic illustration of light rays scattered by a V-shaped etch grain boundary in a polycrystalline material.
Figure 4B:
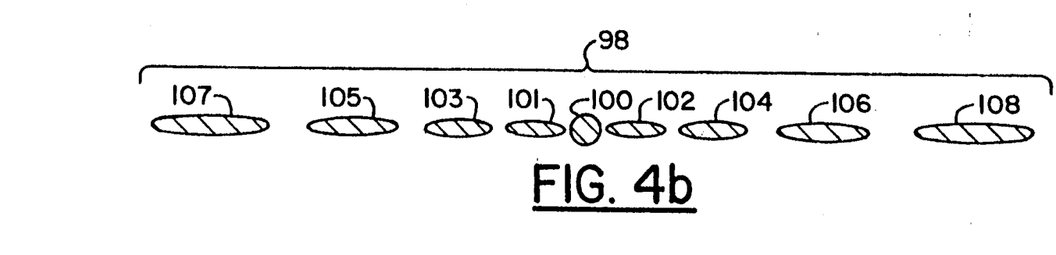

Referring now primarily to FIGS. 4a and 4b, a grain boundary 90 in a polycrystalline material, when etched as described below, will produce a V-shaped groove 92 that is essentially one-dimensional and runs the length of the grain boundary 90 along the surface 20 of the sample 14. Light incident on such etch grain boundaries 90 is scattered in a substantially fan-shaped distribution 94 in a plane that is perpendicular to the surface 20. When the fan-shaped scattered light distribution 94 is projected onto a plane 96 that is parallel to surface 20, it forms a pattern, 98 of divers elongated spots 101, 102, 103, 104, 105, 106, 107, 108 . . . , as illustrated in FIG. 4b. The circular center spot 100 is substantially specular reflection or retroreflection from the V-shaped groove 92 or surface 20.

Referring again, to FIG. 2, a polycrystalline sample 14 is illustrated on X-Y stage 12 with a grain boundary 90 and a V-shaped etch groove 92 where the grain boundary 90 intersects the surface 20, similar to that illustrated in FIG. 4a and described above. The surface 20 also has etch pits 70 where dislocations intersect the surface 20; however, the size and density proportions are not illustrated to scale because of limitations inherent in these kinds of illustrations for microscopic features. As shown in FIG. 2, a fairly wide or large diameter beam 18 is used to illuminate a sufficiently large portion of the surface 20 to obtain a good statistical sample of etch pits. Therefore, there is no attempt to focus the beam 18 to a point on the surface 20. In fact, it is preferred that a point focus is avoided. Generally, it is preferred to include at least two hundred etch pits in the illuminated area, which usually requires a beam 18 diameter of about 500 to 1,000 μm.

Figure 5:
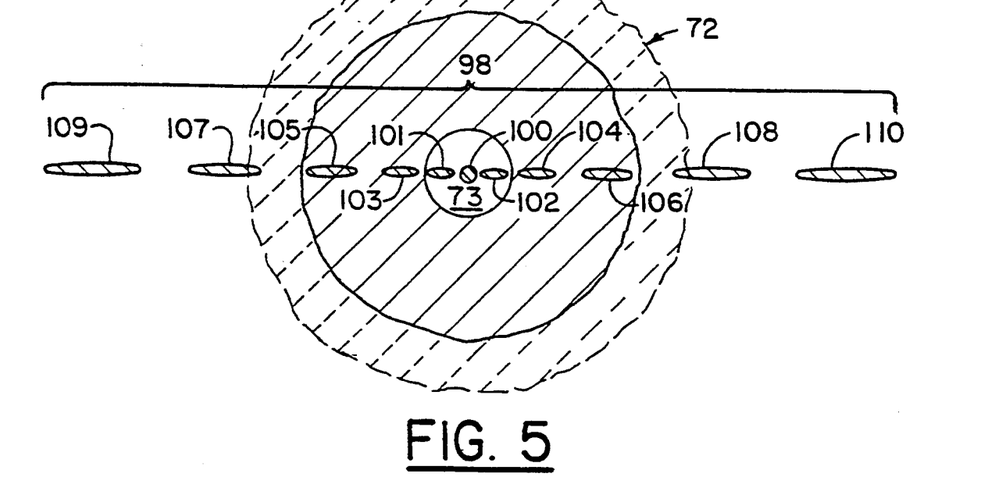
FIG. 5 illustrates the grain boundary light pattern of FIG. 4b superimposed on the etch pit light pattern of FIG. 3b, which combination occurs when a beam illuminating an etch pit sample surface encounters an etch grain boundary, as illustrated in FIG. 2.
Figure 6:
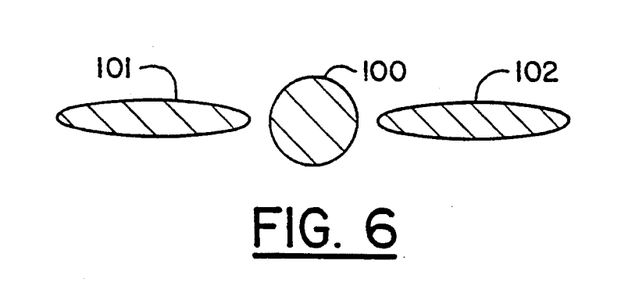
FIG. 6 is an illustration of the central part of the grain boundary scattered light pattern that is captured separate from the etch pitch scattered light according to this invention.

As also shown in FIG. 2 for purposes of illustrating additional features of this invention, the V-shaped grain boundary etch groove 90 is positioned in the area illuminated by beam 18. Consequently, both an etch pit scattered light pattern, such as one of the patterns illustrated in FIGS. 3a through 3h, and a boundary grain etch scattered light pattern, such as the pattern 98 illustrated in FIGS. 4a and 4b, are produced together. The result is a combination etch pit light scattered pattern, such as pattern 72 of FIGS. 3a and 3b, combined with a boundary grain etch pattern 98 of FIGS. 4a and 4b. The combination of these patterns 72 and 98 is illustrated in FIG. 5. The specular components 38 of FIGS. 2 and 4a that produce center spot 100 of FIGS. 4b and 5, and the near specular components 34 and 36 of FIGS. 2 and 4a that produce the inside spots 101 and 102, respectively, of FIGS. 4b and 5 deviate from specular normal for the most pan less than five degrees (5°). Therefore, as best illustrated in FIGS. 2 and 5, those light components 34, 36, and 38 and their corresponding spots. 100, 101, and 102 are for the most part confined in the center area 73 that is substantially devoid of etch pit scattered light 30. Therefore, as shown in FIG. 2, the top aperture 24 of the light integration sphere 22 allows the light components 34, 36 and 38 scattered or reflected by the boundary grain etch groove 90 to pass out of the light integrating sphere 22. Therefore, the limited pattern shown in FIG. 6 comprising only spots 100, 101, and 102 reaches the plane 112 of the center block aperture 44 in FIG. 2. The specular component 38 is subsequently blocked and eliminated from the system 10 by the center block aperture 44 as mentioned above. Consequently, only the near specular light components 34 and 36 scattered by the boundary grain etch groove 90 pass through the light integrating sphere 22 and reach the second photodetector 50. Substantially all of the etch pit scattered light 30 is captured in the light integrating sphere 22, as described above, and is detected only by the first photodetector 40. As a result, the signal produced by the second photodetector 50 is essentially the result of a grain boundary 90 in the area of illumination by beam 18. This signal on lead 52, therefore, can be processed, discriminated, and used for detecting and mapping grain boundaries in polycrystalline materials as distinct from dislocation defects.

Figure 7:
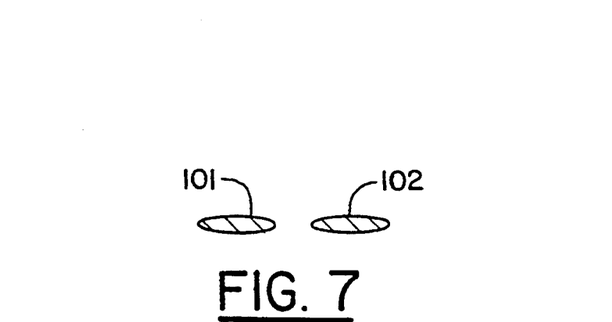
FIG. 7 is an illustration of the grain boundary scattered light pattern of FIG. 6 after removal of the center spot and converging for incidence on a photodetector.

The light components 34, 36, and 38 that pass through the top aperture 24 of light integrating 22 are collimated by a lens 114, reflected out of the normal path by beam splitter or partially silvered mirror 116, and directed to the center block aperture 44. As mentioned above, the projected light components 34, 36, and 38 that reach plane 112 of aperture 44 are substantially as show in FIG. 6. The aperture 44 has an annular opening 45 large enough to pass substantial portions of the near specular components 34 and 36 and a center block 46 large enough to block the specular component 38. A convex lens 118 converges and focuses the near specular components 34 and 36 onto the second detector 50, so that the projection of the light, essentially comprising those near specular components 34 and 36, appears as the near spots 101 and 102, illustrated in FIG. 7, sans the specular component 38 and circular center spot 100. It is important to eliminate the specular component 38, because a substantial portion of the specular component 38 can be, and probably is, light reflected from smooth, nondefect areas of the surface 20 of the polycrystalline material 14 adjacent the grain boundary 90, thus could also be present in the signal from the second photodetector 50, even if there is no grain boundary in the area of illumination. Elimination of the center component 38 insures that the only signal from photodetector 50 is from a grain boundary defect.

It may be noted that the components of the grain boundary scattered light 94, that produce the intermediate spots 103–108 in the pattern 98, as illustrated in FIGS. 4a, 4b, and 5, will not pass through the top aperture 24 of light integrating sphere 22, and thus will be captured along with the etch pit scattered light 30 inside the light integrating sphere 22 of FIG. 2. If those intermediate components of the grain boundary scattered light 94 are intense enough, they can affect and cause erroneous signals of etch pit density (EPD) from the first photodetector 40. In fact, if the beam 18 was narrowed to a point, and if the point was focused on the grain boundary etch 92, the resulting grain boundary scattered light 94 intensity inside the light integrating sphere 22 would probably predominate and could even swamp out any etch pit scattered light intensity. Actually, the first photodetector 40 could operate as a grain boundary 90 detector in that configuration.

On the other hand, the effect of the intermediate components of grain boundary scattered light 94 can be minimized in several ways. First, the incident beam 18 can be operated with a wide diameter; thus illuminating a larger area of etch pit defects 70 on the surface 20 of the polycrystalline material 14. Such wide area illumination increases substantially the intensity of etch pit scattered light 30 inside the light integrating sphere 22 as compared to the grain boundary scattered light 94. Further, since the problem of the grain boundary scattered light 94 is essentially one-dimensional, while the pattern of the etch pit scattered light 30 is two dimensional, a larger area illumination can minimize the effect of the grain boundary scattered light inside the light integrating sphere 22 that is detected by the first photodetector 40. Additional electronic signal conditioning and processing as described below, can further minimize the residual effects of the grain boundary scattered light detected by first photodetector 40.

Another adjustment that can minimize the effects of divers components of grain boundary scattered light 94 is to increase the distance between the bottom aperture 26 of the light integrating sphere 22 and the surface 20 of the polycrystalline material 14. Increasing this distance can allow the fartherest-out components of the grain boundary scattered light 94, which spread at a large angle to normal, i.e., a smaller angle to the surface 20, to pass beneath the light integrating sphere 22 and avoid capture by the bottom aperture 26. Of course, raising the light integrating sphere 22 to an even larger distance off the surface 20 could cause the outer fringes of the etch pit scattered light 30 to be excluded, too, which could be counterproductive. Widening the bottom aperture 26, along with increasing the distance between the light integrating sphere 22 and the surface 20, could help to capture the outer fringes of the etch pit scattered light 30, but wider apertures can also allow diffuse light inside the light integrating sphere 22 to escape, thus lowering intensity and signal strength from the first photodetector 40. Therefore, there is a balance that can be found and maintained between incident beam 18 size, distance between light integrator 22 and size of surface 12, and apertures 24 and 26 that provides optimum results and signals for a particular system 10 used in conjunction with a particular polycrystalline material 14. A larger beam 18 size also increase the size of the increments needed to scan a sample 14, as well as the statistical base of the method used in this invention which detects statistical defect densities, instead of detecting and counting individual etch pits. Therefore, the larger rastor increments along with the increased statistical base of defect densities that result from a larger sized beam 18, as described above, can combine to increase substantially the defect mapping speed and efficiency according to this invention.

Referring again to FIG. 1, the etch pit density (EPD) signal on lead 42 is directed to a final amplifier circuit 120, where it is conditioned, filtered, cleaned up, and amplified. Likewise, the grain boundary signal on lead 52 is directed to a second amplifier circuit 122, where it is also conditioned, filtered, cleaned up, and amplified. Both signals are then directed via leads 124, 126, respectively, to an algebraic summing circuit 128, where the etch pit or dislocation signal is algebraically summed with (subtracted from) the product of an empirically determined constant times the grain boundary signal to produce a new signal that is indicative of grain boundary for mapping purposes. Initialization can be made on a location that is known to be all dislocation defects and no grain boundary defects. In the opposite mode, the grain boundary signal can be algebraically summed with the product of a constant times the dislocation signal to produce a net signal that is indicative of dislocation density.

Figure 9:
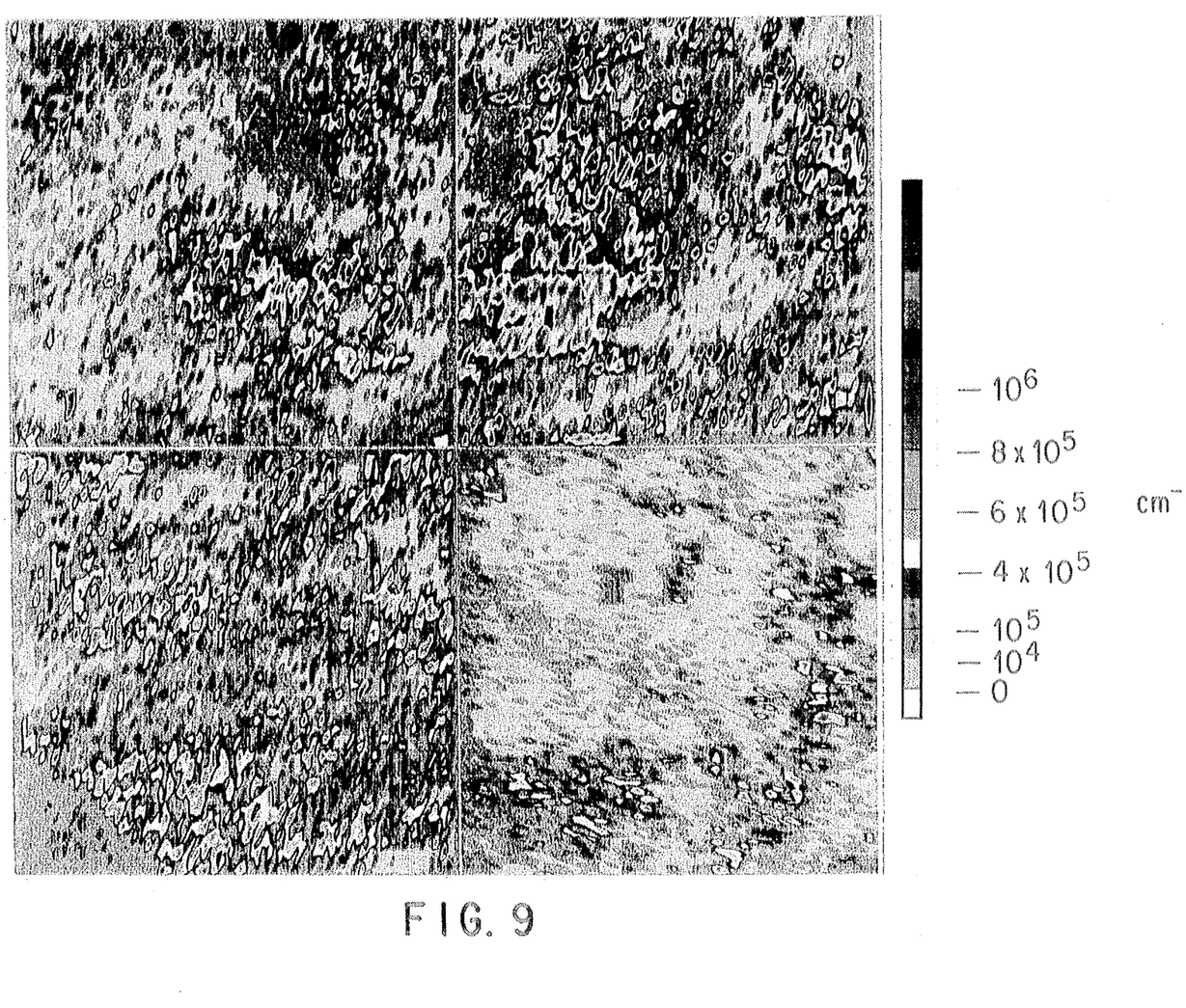
FIG. 9 is a dislocation defect map of a crystal system wafer produced according to this process.
Figure 10A:
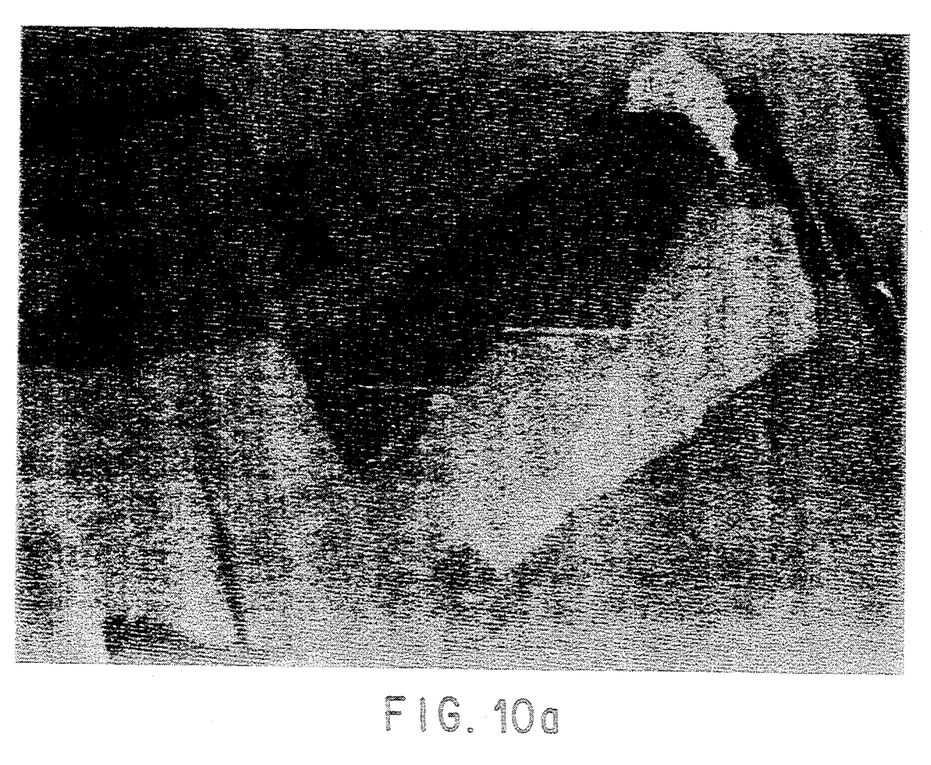
FIG. 10a is a photograph showing the grain boundaries in a surface of polycrystalline silicon wafer.
Figure 10B:
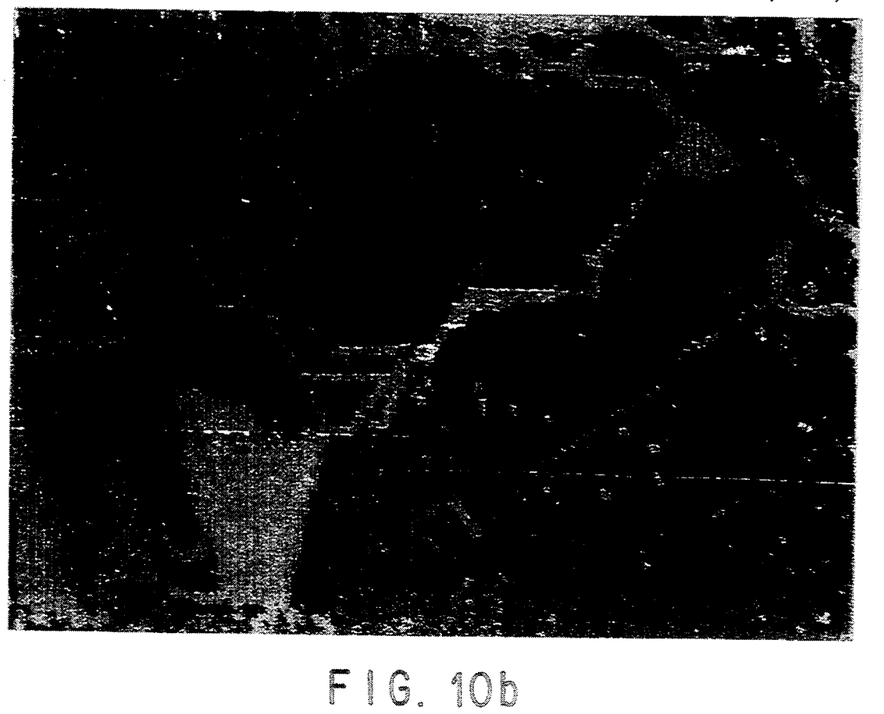
FIG. 10b is a grain boundary defect map of the wafer of FIG. 10a produced according to this invention.

The dislocation density and grain boundary signals are fed into a computer 130 along with X–Y position information from the stage 12 via connection 132. The data are stored in a high-speed buffer memory. Commercially available computer software, such as "Lab View," produced by National Instruments, of 6504 Bridgepoint Parkway, Austin, Tex. 78820 "Delta Graph," produced by Deltapoint, Inc. of 2 Harris Court, Suite B-1, Monterey, Calif. 93940 can be used, with appropriate modifications for particular system hardware and other parameters that would be within the capabilities of persons skilled in this art, to make a map of the dislocation densities and grain boundaries in the material 14, and detailed analysis or displays can be made on the monitor 134 and by a color printer or plotter 136. For example, a defect density map produced with the system 10 according to this invention is shown in FIG. 9. Alternatively, the grain boundary data can be used to produce a grain boundary map. For example, the grain boundaries shown in the microscopic photograph of FIG. 10a was scanned with the system 10 of this invention, and the grain boundary map in FIG. 10b was produced with the data. Alternatively, analog signals from the photodetectors 40 and 50 can be processed by the analog display controller 138 to directly display the dislocation and grain boundary distributions on a storage oscilloscope 140 or an X-Y recorder 142.

The preferred etching process for use with this invention is a variation of the chemical etching procedure published by the inventor in B. L. Sopori, "A New Etch for Polycrystalline Silicon," *J. Electrochem. Soc.*: SO-LID-STATE SCIENCE AND TECHNOLOGY, Vol. 131, No. 3, Page 667 (1984), which produces substantially equal volume etch pits, regardless of dislocation orientation. The following mixtures are used in defect etching:

1) 1:1 of hydrofluoric acid (HF) to water, referred to as the HF rinse.
2) 1:1 of nitric acid ($HNO_3$) to water, referred to as the $HNO_3$ rinse.
3) 36:15:2 of hydrofluoric acid to acetic acid ($CH_3COOH$) to nitric acid, referred to as Sopori etch.
4) 2:1 of sulfuric acid ($H_2O_2$), referred to as Piranha.

The steps of this procedure include:
a) Make sure the sample to be etched is clean by checking it under the microscope. If the sample is not clean (there are blobs visible on the surface), it should be cleaned.
b) Heat the Piranha on the hot plate to 80° C. (a setting of "LOW"). It takes approximately 15–20 minutes to heat the Piranha. It is hot enough when it begins to gently bubble. Do not let the Piranha reach a fun boil. If the Piranha was just mixed it does not need to be heated; the heat generated in mixing the $H_2SO_4$ and $H_2O_2$ is adequate.
c) Place the sample in a Teflon sample holder and then let the sample sit in the Piranha for 15 to 30 minutes. The Piranha cleans off any remaining small bits of wax or dirt on the surface of the sample. After the sample has soaked, rinse it off with a stream of deionized (DI) water and blow it dry with the air gun.
d) The HF rinse, the $HNO_3$ rinse, and the etch should be poured from their storage bottles into separate, labeled, plastic one-liter beakers. Fill a two-liter beaker with DI water for rinsing the samples after etching.
e) Dip the sample into the etch and gently wave it back and forth for approximately 30 seconds after bubbles begin to form. Remove the sample from the etch and immediately dip it into the beaker of DI water. Gently wave the sample back and forth for several seconds and theft rinse it with a stream of DI water. Dry the sample with the air gun.
f) Dip the sample in the $HNO_3$ rinse and gently wave it back and forth for approximately 15 seconds. Remove the sample and dip it into the beaker of DI water for several seconds. Rinse the sample in a stream of DI water and then dry it with the air gun.
g) Dip the sample in the HF rinse and wave it back and forth for approximately 15 seconds. Remove the sample and dip it into the beaker of DI water for several seconds. Rinse the sample in a stream of DI water and then dry it with the air gun.
h) After etching, the HF rinse, the $HNO_3$ rinse, and the etch should be poured back into their storage bottles. The bottles should then be placed together in the square Nalgene secondary container labeled in the "Defect Etching and Chem Polishing" in the acid hood. Replace the cover on the secondary container. The Piranha should be left on the hot plate and covered after it has cooled.
i) Using DI water, rinse out the beakers from the HF rinse, the $HNO_3$ rinse, and the etch. Place the beakers upside down in the back right hand corner of the hood (by the sink) to dry. Wipe off the acid hood countertop.
j) Make an entry in the Etch log stating the date, your initials, the number of samples you etched, and any general comments about what happened when you etched.

There is not as yet a set number of times that the HF rinse, the $HNO_3$ rinse, the etch, and the Piranha can be reused. Part of the purpose of the Etch Log is to establish this time.

Figure 11:
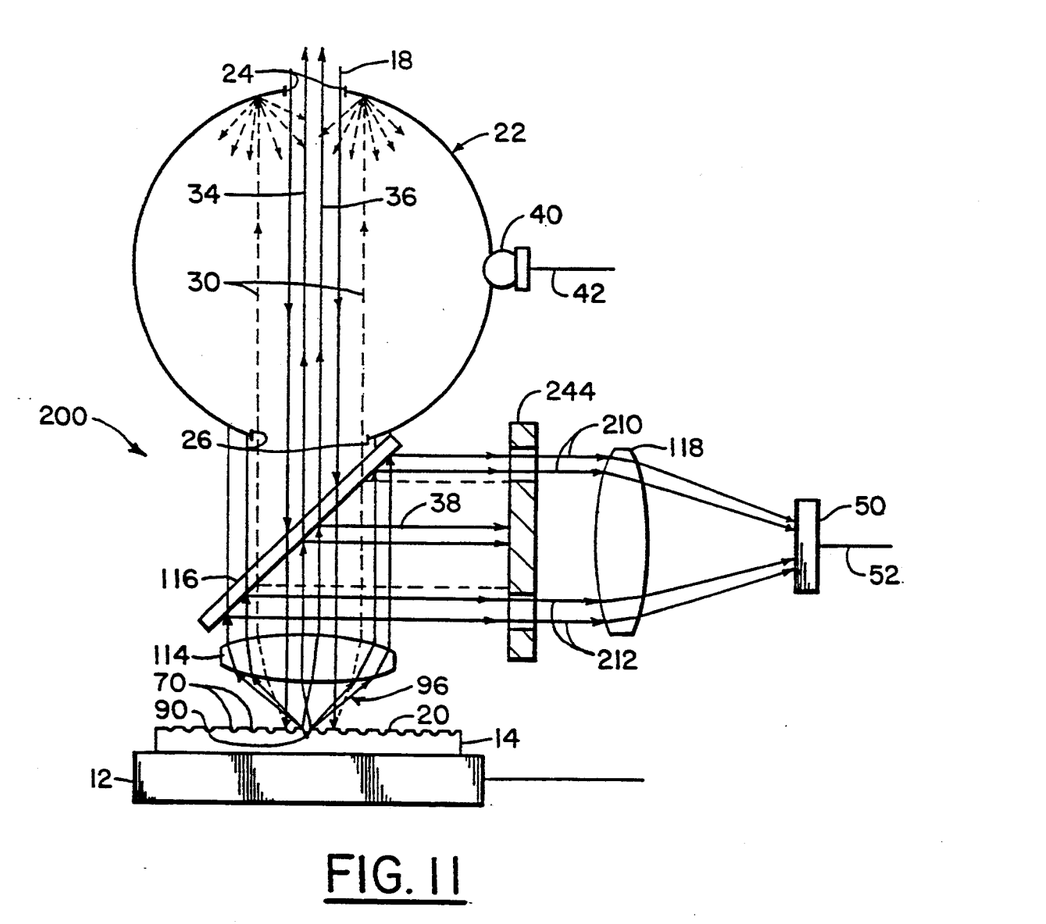
FIG. 11 is a schematic diagram of an alternate embodiment defect mapping system according to the present invention.

An alternate embodiment system 200 is shown in FIG. 11. In this embodiment, the light integrating sphere 22 is positioned far enough away from the surface 20 to accommodate the collimating lense 114 and beam splitter 116 between the light integrating sphere 22 and surface 20. The beam splitter 116 diverts pan of the grain boundary scattered light 96 and etch pit scattered light 30 toward the second photodetector 50 before reaching the light integrating sphere 22. In this embodiment, the blocking aperture 244 passes only the outer portions 210 and 212 of the grain boundary scattered light 96 to the second detector 50 and blocks everything else. The bottom aperture 26 of light integrating sphere 22 is large enough to admit the etch pit scattered light 30, but small enough to block the outer portions of grain boundary scattered light 96 that passes through beam splitter 116. The near specular portions 34 and 36 of grain boundary scattered light 96 that pass through the beam splitter 116 also pass out the to aperture 24 of light integrating sphere 22. Therefore, it is only the intermediate portions of grain boundary scattered light that enters and gets captured in the light integrating sphere 22 along with the etch pit scattered light 30. This intermediate portion of grain boundary scattered light, as in the embodiment 10 described above, is not sufficient to swamp or degrade the intensity signal for etch pit scattered light 30 as long as the incident beam 18 illuminates a wide enough area on surface 20.

The foregoing description is considered as illustrative only of the principles of the invention. Furthermore, since numerous modifications and changes will readily occur to those skilled in the art, it is not desired to limit the invention to the exact construction and process shown as described above. Accordingly, all suitable modifications and equivalents may be resorted to falling within the scope of the invention as defined by the claims which follow.

The embodiments of the invention in which an exclusive property or privilege is claimed are defined as follows:

1. A method for detecting and distinguishing between a first type of defect and a second type of defect in the surface of a crystalline material, comprising the steps of:

preparing said surface in such a manner that said first type of defect scatters incident light in a first pattern and said second type of defect scatters incident light in a second pattern;

illuminating said surface with incident light and scattering said incident light from said surface to create said first pattern and said second pattern;

separating at least some of the scattered light in said first pattern from at least some of the scattered light in the second pattern;

detecting the scattered light of said first pattern as an indication of said first type of defect in the surface of the crystalline material;

and detecting the scattered light of said second pattern as an indication of said second type of defect in the surface of the crystalline material.

2. The method of claim 1, including the step of preparing said surface in such a manner that:

said first type of defect scatters incident light in a first pattern that has an area of intense scattered light and an area of substantially no scattered light; and said second type of defect scatters incident light in a second pattern that at least partially occupies said area in said first pattern that has substantially no scattered light from said first type of defect.

3. The method of claim 2, including the step of preparing said surface in such a manner that:

said first type of defect scatters incident light in a first pattern that would project a primarily two-dimensional image shape on an intersecting plane; and said second type of defect scatters incident light in a second pattern that would project a primarily one-dimensional image shape on an intersecting plane.

4. The method of claim 3, including the step of detecting the scattered light of said second pattern that is in said area of no substantially scattered light in said first pattern as an indication of the presence of said second type of defect in the surface of the crystalline material that is illuminated.

5. The method of claim 4, including the steps of:

capturing most of the scattered light in said first pattern in a light integrating sphere and creating an integrated diffuse light in said sphere while substantially precluding the scattered light of said second pattern that is in said area of substantially no uttered light in said first pattern from being captured in said light integrating sphere; and detecting diffuse light in said light integrating sphere as an indication of the presence of said first type of defect in the surface of the crystalline material that is illuminated.

6. The method of claim 5, including the steps of illuminating a portion of said surface of said crystalline material that is large enough to cause the scattered light in the first pattern to substantially swamp any scattered light in said second pattern that gets captured in said light integrating sphere such that the diffuse light detected in said light integrating sphere is practically an indication of only said first type of defect in said surface of said crystalline material.

7. The method of claim 6, including the steps of preparing said surface in such a manner that said first type of defect scatters incident light in said first pattern that has an area of intense scattered light in an intermediate specular range and an area of substantially no scattered light in a specular range and a near specular range.

8. The method of claim 7, including the step of preparing said surface in such a manner that said second type of defect scatters incident light in said second pattern that has at least some scattered light in said near specular range.

9. The method of claim 8, including the step of capturing most of the scattered light in the intermediate specular range in said light integrating sphere and allowing most of the scattered light in said near specular range to pass through the light integrating sphere.

10. The method of claim 9, including the step of detecting the scattered light that passes through said light integrating sphere as an indication of the presence of a second type of defect in the surface of said crystalline material.

11. The method of claim 10, including the step of blocking light in the specular range that passes through said light integrating sphere from being detected along with the light in the near specular range.

12. The method of claim 7, including the step of preparing said surface in such a manner that said second type of defect scatters incident light in said second pattern that has at least some scattered light in a far specular pattern.

13. The method of claim 12, including the step of capturing most of the scattered light in the intermediate specular range in said light integrating sphere and precluding most of the scattered light in said far specular region from entering said light integrating sphere.

14. The method of claim 13, including the step of detecting the scattered light that is precluded from entering the light integrating sphere as an indication of the presence of said second type of defect in the surface of the crystalline material.

15. The method of claim 5, including the step of illuminating a portion of said surface of said crystalline material that is small enough that there is insufficient light scattered from said first type of defect to prevent light scattered from said second type of defect from causing substantial changes in diffuse light detected in said light integrating sphere such that a substantial increase in diffuse light detected in tile light integrating sphere can indicate a second type defect in the area of the surface of the crystalline material that is illuminated.

16. The method of claim 1, including tile step of preparing said surface in such a manner that dislocation defects in the surface of the crystalline material scatter light in said first pattern.

17. The method of claim 16, including the step of preparing said surface in such a manner that etch pits of about equal volume are created at substantially all dislocation defects that interest said surface.

18. The method of claim 1, including the step of preparing said surface in such a manner that grain boundary defects at the surface of the crystalline material scatter light in said second pattern.

19. The method of claim 1, including the steps of:

selecting silicon as the crystalline material;

cleaning the surface of the crystalline material by application of a mixture of sulfuric acid and hydrogen peroxide;

dipping the crystalline material in an etch solution comprising hydrofluoric acid, acetic acid, and nitric acid to create etch pits at dislocation sites and V-grooves at grain boundary sites in said surface;

rinsing the crystalline material in nitric acid to form a silicon dioxide coating on the surface;

applying hydrofloric acid rinse to the crystalline material; and rising the crystalline material with water.

20. The method of claim 1, including the steps of:

detecting said first type of defect and said second type of defect at a plurality of locations on said surface;

collecting and recording information relating to said first type of defect and said second type of defect at each location in conjunction with information that identifies the position of each location in relation to the positions of other ones of the locations;

creating a map of the surface of the crystalline material using the defect type and location information that displays either the first type of defect, the second type of defect, or both the first and second types of defects in scaled spatial relation to each other.

* * * * *